United States Patent [19]

Ma et al.

[11] Patent Number: 5,574,056
[45] Date of Patent: Nov. 12, 1996

[54] FUNGICIDAL AZOLE DERIVATIVES

[75] Inventors: Shih-Yu Ma; Robert A. Davis, both of Cheshire, Conn.

[73] Assignee: Uniroyal Chemical Company, Inc., Middlebury, Conn.

[21] Appl. No.: 464,439

[22] Filed: Jun. 5, 1995

Related U.S. Application Data

[62] Division of Ser. No. 234,856, Apr. 28, 1994.

[51] Int. Cl.$^6$ ........................ A01N 43/653; C07D 405/06
[52] U.S. Cl. ........................ 514/383; 514/340; 546/340; 546/272.4; 546/272.7; 546/275.1; 546/281.7; 548/262.2; 548/267.8; 548/268.4; 548/268.6
[58] Field of Search ........................ 546/276; 548/262.2, 548/267.8, 268.4, 268.6; 514/340, 383

[56] References Cited

U.S. PATENT DOCUMENTS 4,507,140  3/1985  Sugauanam ............................. 71/76

FOREIGN PATENT DOCUMENTS 3813841  12/1988  Germany.

*Primary Examiner*—Patricia L. Morris
*Attorney, Agent, or Firm*—Daniel Reitenbach

[57] ABSTRACT

Compounds having the formula

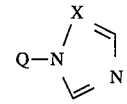

wherein Q is

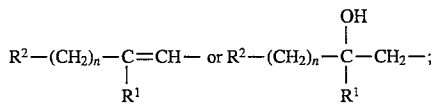

$R^1$ is $C_1$–$C_8$ alkyl;

$R^2$ is $C_6$–$C_{18}$ aryl, unsubstituted or substituted with one or more $C_1$–$C_6$ alkyl, halo, $C_1$–$C_6$ alkoxy or $C_1$–$C_6$ haloalkyl; or $C_4$–$C_{17}$ heterocyclic aryl comprising one or more oxygen or nitrogen atoms;

X is nitrogen or —CH—; and n is 2, 3 or 4, or a stereoisomer thereof, with the proviso that when Q is

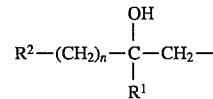

and X is N, then $R^2$ is not phenyl or substituted phenyl. These compounds are useful as fungicides.

9 Claims, No Drawings

FUNGICIDAL AZOLE DERIVATIVES

FIELD OF THE INVENTION

This is a division of application Ser. No. 08/234,856, filed Apr. 28, 1994.

The present invention is related to novel substituted azole derivatives. More particularly, the present invention is related to novel substituted imidazole and triazole derivatives having a broad spectrum of fungicidal activity.

BACKGROUND OF THE INVENTION

The control of phytopathogenic fungi is important because fungal growth on plants or plant parts, such fruits, blossoms, foliage, stems, tubers, and roots, inhibits the production of foliage, fruit or seed, and reduces the overall quality of the harvested crop.

Certain compounds have been described as useful for the control of phytopathogenic fungi. For example, U.S. Pat. No. 4,626,594 describes a process for preparing beta-hydroxyethyl-(1,2,4-triazole) derivatives, which are said to have fungicidal activity. European Patent Application 63,099 describes 1-triazolyl-2-phenylalkane compounds said to be useful as fungicides. European Patent Application 60,223 describes 1-styrylimidazole and 1,2,4-triazole derivatives said to have fungicidal activity. European Patent Application 79,856 describes 1-styryl-1,2,4-triazole derivatives said to have fungicidal use.

It is an object of this invention to provide novel azole derivatives having a broad spectrum of fungicidal activity.

It is also an object of this invention to provide novel fungicidal compositions comprising the novel azole derivatives.

Additionally, it is a further object of this invention to provide a method for controlling undesirable fungi using the novel azole derivatives.

SUMMARY OF THE INVENTION

The present invention relates to a compound of the formula:

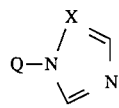

wherein Q is

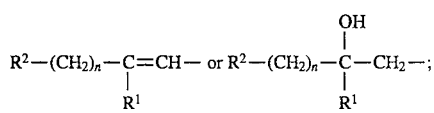

$R^1$ is $C_1$–$C_8$ alkyl;
$R^2$ is $C_6$–$C_{18}$ aryl, unsubstituted or substituted with one or more $C_1$–$C_6$ alkyl, halo, $C_1$–$C_6$ alkoxy or $C_1$–$C_6$ haloalkyl; or $C_4$–$C_{17}$ heterocyclic aryl comprising one or more oxygen or nitrogen atoms;
X is nitrogen or —CH—; and
n is 2, 3 or 4, or a stereoisomer thereof, with the proviso that when Q is

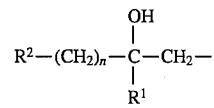

and X is N, then $R^2$ is not phenyl or substituted phenyl. These compounds are useful as fungicides.

In particular, one aspect of the present invention relates to a compound of the formula:

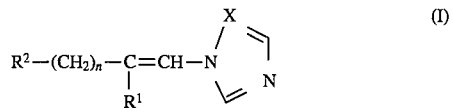

wherein n, X, $R^1$ and $R^2$ are as defined above.

The present invention also relates to compounds of the formula:

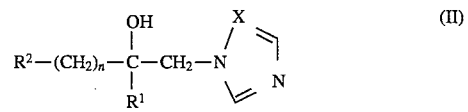

wherein n, $R^1$, $R^2$ and X are as defined above. The compounds of formula II are useful as fungicides and as intermediates in the production of the compounds of formula I.

The present invention is also related to fungicidal compositions comprising: a) a fungicidally effective amount at least one compound of formula I or II above, and b) a suitable carrier.

The present invention is additionally related to a process for controlling undesirable fungi which comprises applying a fungicidally effective amount of at least one compound or composition of the present invention, to a locus to be protected.

DETAILED DESCRIPTION OF THE INVENTION

Preferred compounds of this invention are the compounds of formula I or formula II wherein:
n is 2;
$R^1$ is $C_3$–$C_6$ alkyl;
$R^2$ is $C_6$–$C_{12}$ aryl, unsubstituted or substituted with one or more $C_1$–$C_4$ alkyl, halo, $C_1$–$C_4$ alkoxy or $C_1$–$C_4$ haloalkyl; or $C_5$–$C_{10}$ heterocyclic aryl comprising one or more oxygen or nitrogen atoms; and
X is nitrogen or —CH—.
Particularly preferred are those compounds wherein:
n is 2;
$R^1$ is $C_3$–$C_6$ branched alkyl;
$R^2$ is phenyl, phenyl substituted with $C_1$–$C_4$ alkyl, halo, $C_1$–$C_4$ alkoxy or $C_1$–$C_4$ haloalkyl, biphenyl, naphthyl, pyridyl, benzodioxolyl or benzodioxolanyl; and
X is nitrogen.
Most preferred are those compounds wherein:
n is 2;
$R^1$ is t-butyl;
$R^2$ is phenyl, phenyl substituted with $C_1$–$C_4$ alkyl, chloro, fluoro, $C_1$–$C_4$ alkoxy, $C_1$–$C_4$ chloroalkyl or $C_1$–$C_4$ fluoroalkyl, biphenyl, naphthyl, pyridyl, benzodioxolyl or benzodioxolanyl; and
X is nitrogen.

The compounds of the present invention can be prepared by the methods described below.

One method for the preparation of the compound of formula I (Process A) can be represented as follows:

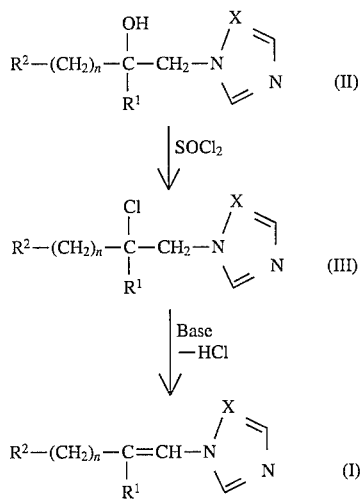

wherein n, R¹, R² and X are as defined above.

In this process, the compound of formula II is chlorinated with thionyl chloride to produce a compound of formula III, which is then dehydrochlorinated by either an organic base such as triethyl amine, or an inorganic base such as sodium carbonate, to produce the compound of formula I. Representative compounds of formula I are listed in Table 1, with structure and characterizing data provided.

A method which is useful for the preparation of the compounds of formula II (Process B), can be represented as follows:

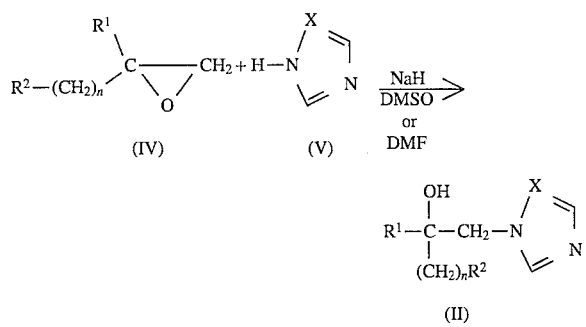

wherein n, R¹, R² and X are as defined above.

In this method, an oxirane of formula IV is reacted with an azole of formula V and a base, such as sodium hydride, in an aprotic solvent, such as N,N,-dimethylformamide or dimethylsulfoxide, to produce a compound of formula II.

An alternate method for preparing the compound of formula I (Process C) can be represented as follows:

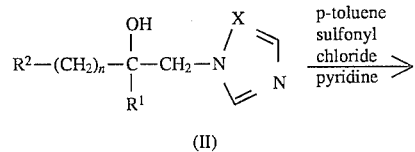

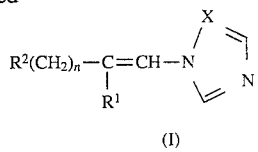

wherein n, R¹, R² and X are as defined above.

In this method, the compound of formula II is treated with p-toluenesulfonyl chloride to form the corresponding tosylate. In the presence of a base such as pyridine, the p-toluenesulfonic acid is eliminated, to produce the compound of formula I.

Another method for preparing the compound of formula I (Process D) can be represented by the following:

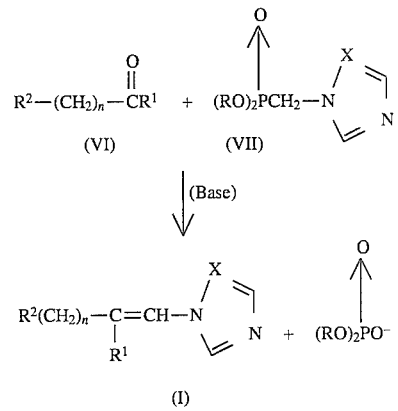

wherein n, R¹, R² and X are as defined above, and R is alkyl.

In this method, a ketone of formula VI is reacted with an ylide generated from a diethyl(1H-1,2,4-triazol- 1-yl)methyl phosphonate of formula VII, in the presence of a base, to produce the compound of formula I. This method is a Wadsworth-Emmons modification of the Wittig reaction to synthesize olefinic structures. The Wittig reaction is a well-known method of synthesizing alkenes from carbonyl compounds. See, e.g., W. S. Wadsworth, Jr. and W. D. Emmons, "The utility of phosphonate carbanions in olefin synthesis", J. Am. Chem. 83, 1733 (1961). This method produces a regiospecific (exclusively one of two possible isomeric products) product similar to that synthesized by Process A.

The synthetic details of the methods described above as well as preferred reagents and reaction conditions are provided in the Examples that follow.

The compounds of formula I or II can also form salts with organic and inorganic acids. These salts can be obtained by known methods for salt formation, for example, by dissolving a compound of formula I or II in a suitable inert solvent and adding an acid. Diethylether and toluene are examples of two common solvents. The resulting salts can then be isolated by any known method, such as by filtration and, if appropriate, purification by washing in an inert organic solvent. The physiologically acceptable salts are also intended to be within the scope of this invention.

It should be noted that certain compounds of formula I may exist as a mixture of E and Z isomers. Such isomers are not necessarily separated and their mixture is also intended to be within the scope of this invention.

Another aspect of the present invention is a composition which comprises a fungicidally effective amount of the compound of formula I or formula II, and a suitable carrier therefor. Suitable carriers useful in the composition of this invention can be agriculturally acceptable liquids, solids or mixtures thereof.

A liquid carrier useful in the composition of this invention, can be a solvent or a dispersant. In addition, two liquid carriers can be utilized, one serving as a solvent and the other as a dispersant.

In a preferred embodiment wherein the composition is a solution, the solvent carrier is usually an organic compound which may be polar or non-polar. Useful solvents include acetone, methanol, isopropanol, t-butyl alcohol, cyclohexanone, n-butyl alcohol, toluene, xylene, dioxane, dimethylformamide, dimethylsulfoxide, ethylene dichloride and N-methylpyrrolidone.

Another type of liquid composition within the contemplation of this invention is an emulsion. An emulsion is formed when the compound of formula I or formula II, is dispersed in water in the presence of a surface active agent. An emulsion is preferably formed by first preparing a solution of the type discussed in the above paragraph. The solution is then dispersed in water and a surface active agent is added thereto to form the emulsion. Surface active agents suitable for use in forming an emulsion useful in the composition of this invention, can be anionic, cationic or non-ionic, and are known in the art. *McCutcheon's Detergents and Emulsifiers,* Allured Publishing Corp., Ridgewood, N.J. (1970); U.S. Pat. No. 2,514,916 and U.S. Pat. No. 2,547,734, describe surface active agents useful in forming emulsions useful in the compositions of this invention.

A third type of liquid composition within the scope of this invention comprises a liquid dispersant as the carrier. In this embodiment, the compound of formula I or formula II, is dispersed in water in the absence of a surface active agent. Alternatively, the liquid composition comprises a solution of the compound of formula I or formula II, which, in turn, is dispersed in water, again in the absence of a surface active agent.

A fourth type of liquid composition within the scope of this invention, utilizes an aerosol. An aerosol is liquid under pressure but is gaseous at atmospheric pressure and ambient temperature. In most instances, an aerosol composition is prepared by first forming a solution of the compound of formula I or formula II in a conventional solvent of the type discussed above. This solution is then admixed with a volatile liquid aerosol under pressure in which condition the composition is applied.

Solid carriers useful in the composition of this invention include dusts, granules, wettable powders, pastes and water soluble solids. For example, compositions useful in this invention can be applied as a dust when the compound of formula I or formula II is adsorbed or absorbed onto or mixed with a powdered, solid carrier. A solid carrier such as a mineral silicate, e.g., mica, talc, pyrophyllite and clays, can be utilized for this purpose.

Additional solid compositions can be prepared from granular formulations of the compound of formula I or formula II and a granular or pelletized form of carrier such as granular clay, vermiculite, charcoal, corncobs, or the like. The use of granular formulations is particularly suitable for application by broadcasting, side-dressing, soil incorporation or seed treatment.

A mixture of a solid and liquid compostion that employs both a liquid and a solid carrier, can also be used. Such a composition, for example, is prepared by dispersing a solid, on which the compound of formula I or formula II is absorbed or adsorbed, in a liquid dispersant. Such a composition preferably includes a surface active agent to maintain the solid particles dispersed in the liquid dispersant.

The composition of the present invention can utilize a carrier which is itself active. That is, the carrier may be a plant growth regulant, an insecticide, an acaricide, a fungicide, a bacteriacide, or the like.

The concentration of the compound of formula I or formula II in the composition of this invention is a fungicidally effective amount. The exact concentration of the fungicidally effective amount depends upon such factors as the specific plant or plants which are to be protected, the fungus or fungi which are to be controlled, soil conditions and chemistry, and the climatic conditions under which the plant is grown. Generally, the concentration of the compound of formula I or formula II, which is representative of a fungicidally effective amount, in the composition can range from about 0.1% to about 95% by weight. However, when the compound of formula I or formula II is applied as a spray, the dilution can by very high, resulting in a concentration as low as a few parts per million parts of composition. On the other hand, when ultra-low volume applications are employed, full strength concentrates can be utilized.

The compounds and compositions of the present invention can be used in a method for controlling phytopathogenic fungi. In this method, the compound of formula I or formula II is applied to the locus to be protected in a fungicidally effective concentration.

Preferably, the compound of formula I or formula II is applied to the foliage of the plants to be protected ("foliar treatment"). Preferably the foliar treatment is applied at a concentration of between about 10 and about 500 milligrams of the compound of formula I or formula II per liter of inert liquid carrier.

In another preferred embodiment of the present method, a fungicidally effective amount of the compound of formula I or formula II, is applied to the soil in which the plants to be protected from the fungi are grown ("systemic treatment"). Preferably the systemic treatment is applied at a concentration of between about 0.125 and about 10 kilograms of the compound of formula I or formula II per hectare (kg/ha) of soil. More preferably, the compound is applied at a concentration of between about 0.125 kg/ha to about 5 kg/ha.

The application of the compound or composition of the present invention, either by foliar or systemic treatment, can be applied prior to or after infection by fungi. Furthermore, it should be appreciated that the exact dosage, applied systemically or to the foliage, is dictated by the fungus to be controlled and the particular plant to be protected.

In another embodiment of the present method, the compound of formula I or formula II is applied as a coating to the seeds of the plant to be protected. This method provides the benefits of both the foliar treatment and systemic treatment described above. The fungicidal coating protects the plant from infection by the fungi and is also taken up by the plant systemically to protect the plant from fungal attack. In this so-called "seed coating method," a preferred concentration of the active ingredient is in the range of between about 5 and about 75 grams per hundred kilograms of seed.

The following examples are provided to illustrate the present invention.

EXAMPLES

Example 1

Preparation of
1-(1H-1,2,4-triazol-1-yl)-3,3-dimethyl-2-
(4-chlorophenylethyl)-butene (Compound 1 of
Table 1) by Process D A solution of diethyl (1H-1,2,4-triazol-1-yl) methyl phosphonate (6.6 g) in ethylene glycol dimethyl ether (15 ml)

was added dropwise to a stirred slurry of sodium hydride (1.2 g of 60% dispersion in mineral oil) under a nitrogen blanket at a temperature of about 7° C. After stirring for an additional 2 hours at room temperature, the reaction mixture was cooled to 7° C. and then 1-(4-chlorophenyl)-4,4-dimethyl-3-pentanone (6.74 g) was added. [Liquid-phase hydrogenation of alpha, beta unsaturated ketones is described by Cabello et al in J. Org. Chem. 51, 1786, (1986)] The reaction mixture was then gradually heated to 30°–47° C. for 20 hours. A sticky material was formed which prevented efficient stirring by the magnetic stirrer.

The reaction mixture was then poured into ice water (100 ml), extracted with three 60 ml portions of methylene chloride, washed with two 40 ml portions of water, dried over anhydrous magnesium sulfate, and concentrated to give a pale yellow oil (9.0 grams).

NMR analysis indicated a mixture of 1-(1H-1,2,4-triazol-1-yl)-3,3-dimethyl-2-(4-chlorophenyl ethyl)-1-butene (45.4%) and 1-(4-chlorophenyl)-4,4-dimethyl- 3-pentanone (54.6%).

The desired product, 1-(1H-1,2,4-triazol-1-yl)-3,3-dimethyl-2-(4-chlorophenylethyl)-1-butene was isolated by flash column chromatography using silica gel and ethyl acetate/hexane (at 2:8 ratio) mixture as eluant.

A sample of 8.5 g of the reaction mixture gave (i) the recovered starting ketone (3.8 g), and (ii) the E-isomer of the title compound (3.3 g of a solid, m.p. 68°–69° C.). The NMR data for this compound is presented in Table 1.

Example 2

Preparation of 1-(1H-1,2,4-triazol-1-yl)-3,3-dimethyl-2-(4-chlorophenylethyl)-1-butene (Compound 1 of Table 1) by Process A To a stirred solution of alpha-[2-(4-chlorophenyl)ethyl]-alpha-[1,1-dimethylethyl]-1H-1,2,4-triazo-1-yl-ethanol (36 g) in 270 ml of chloroform, thionyl chloride (70 ml) was added dropwise. An exotherm to 35° C. occured. The reaction mixture was further heated at 63° C. for 4 hours. Then, an additional 70 ml of thionyl chloride was added and heated at 68° C. for 2 hours.

The reaction mixture was distilled to remove most of the excess thionyl chloride. The viscous residue was then dissolved in 400 ml of methylene chloride followed by the addition of triethylamine (200 ml) and heated at 47° C. for 3 hours. The reaction mixture was washed with water twice, using 400 ml for each washing.

Concentration gave a viscous residue which was further dissolved in 300 ml of ethyl acetate, washed with brine, dried over anhydrous magnesium sulfate and concentrated again to yield 43.7 g of crude product. The crude product was purified by flash column chromatography (silica gel) using ethyl acetate:hexane in 1:3 proportions as eluant to give 21.5 g, or 63.4% yield, of the title compound as an amber liquid. $^1$H NMR data is presented in Table 1.

The other compounds listed in Table 1 below were prepared using similar procedures to those described above.

TABLE 1

$$R^2-CH_2-CH_2-\underset{R^1}{C}=CH-N\diagdown X \diagdown N$$

| No. | R$_2$ | R$_1$ | X | m.p.(°C.) | NMR Data (CDCl$_3$, ppm) |
|---|---|---|---|---|---|
| 1 |  —⟨⟩—Cl | t-butyl | N | 68–69 | 1.21(S, 9H), 2.56(m, 4H), 6.75(S, 1H), 7.03(d, 2H, J=8.34), 7.20(d, 2H, J=8.43), 8.06(S, 1H), 8.15(S, 1H) |
| 2 | 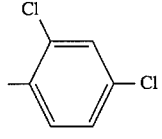 Cl —⟨⟩—Cl | t-butyl | N | 67–69 | 1.24(S, 9H), 2.61(m, 4H), 6.76(S, 1H), 7.04(d, 2H), J=8.16), 7.14(d, d, 1H, J=9.27+2.1), 8.07(S, 1H), 8.16(S, 1H) |
| 3 | 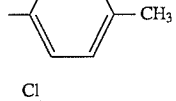 —⟨⟩—CH$_3$ | t-butyl | N | 44–45.5 | 1.24(S, 9H), 2.30(S, 3H), 2.54(m, 4H), 6.74(S, 1H), 6.98(d, 2H), J=8.01), 7.07(d, 2H, J=7.83), 8.06(S, 1H), 8.13(S, 1H) |
| 4 | 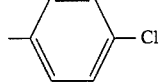 Cl —⟨⟩—Cl | t-butyl | —CH— | 128–129 | 1.98(S, 9H), 2.34(m, 2H), 2.51(m, 2H), 6.81(d, 2H), 7.12(m, 2H), 7.26(m, 2H) |
| 5 | 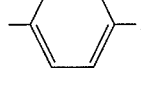 —⟨⟩—F | t-butyl | N | liquid | 1.21 (S, 9H), 2.55(m, 4H), 6.73(S, 1H), 6.91(m, 2H), 7.02 (m, 2H), 8.04(S, 1H), 8.13(S, 1H) |

TABLE 1-continued $$R^2-CH_2-CH_2-\underset{R^1}{C}=CH-N\diagup\overset{X}{\underset{N}{\diagdown}}$$

| No. | R₂ | R₁ | X | m.p.(°C.) | NMR Data (CDCl₃, ppm) |
|---|---|---|---|---|---|
| 6 | ![4-methoxyphenyl]—⟨C₆H₄⟩—OCH₃ | t-butyl | N | liquid | 1.22(S, 9H), 2.55(m, 4H), 3.76(S, 3H), 6.73(S, 1H), 6.79(d, 2H, J=8.61Hz), 6.99(d, 2H, J=8.49Hz), 8.06(S, 1H), 8.14(S, 1H) |
| 7 | biphenyl-4-yl | t-butyl | N | 112–113 | 1.25(S, 9H), 2.62(m, 4H), 6.76(S, 1H), 7.15–7.55(m, 9H), 8.09(S, 1H), 8.17 (S, 1H) |
| 8 | pyridin-2-yl | t-butyl | N | liquid | 1.27(S, 9H), 2.76(S, 4H), 6.79(S, 1H), 7.04(m, 2H), 7.56(m, 1H), 8.51 (d, 1H), 8.03(S, 1H), 8.30(S, 1H) |
| 9 | 1,3-benzodioxol-5-yl | t-butyl | N | liquid | 1.22(S, 9H), 2.47(m, 2H), 2.55(m, 2H), 5.90(S, 2H), 6.52(d, 1H, J=7.8 Hz), 6.59(d, 1H, J=1.6 Hz), 6.69(d, 1H, J=7.8 Hz), 6.74(S, 1H), 8.07(S, 1H), 8.15(S, 1H) |
| 10 | naphthalen-1-yl | t-butyl | N | liquid | 1.28(S, 9H), 2.74(m, 2H), 2.99(m, 2H), 6.80(S, 1H), 7.26–7.85 (m, 7H), 8.14(S, 1H), 8.18(S, 1H) |
| 11 | naphthalen-2-yl | t-butyl | N | 85–87 | 1.21(S, 9H), 2.68(S, 4H), 6.78(S, 1H), 7.21(d, d, 1H), 7.39(m, 2H), 7.51(S, 1H), 7.73(m, 3H), 8.11(S, 1H), 8.14(S, 1H) |
| 12 | 4-tert-butylphenyl —⟨C₆H₄⟩—C(CH₃)₃ | t-butyl | N | 70–71.5 | 1.23(S, 9H), 1.29(S, 9H), 2.52(m, 4H), 6.74(S,1 H), 7.02(d, 2H, J=8.1 Hz), 7.28(d, 2H, J=8.1 Hz), 8.06(S, 1H), 8.13(S, 1H) |
| 13 | 4-(trifluoromethyl)phenyl —⟨C₆H₄⟩—CF₃ | t-butyl | N | 71–73 | 1.22(S, 9H), 2.62(S, 4H), 6.76(S, 1H), 7.20(d, 2H, J=7.9 Hz), 7.50(d,2H, J=7.9 Hz), 8.06(S, 1H), 8.15(S, 1H) |

Example 3

Preparation of α-[2-(1,3-benzodioxol-5-yl)ethyl]-α-1,1-dimethylethyl-2-(1H-1,2,4-triazol-1-yl)ethanol (Compound 16 of Table 2) by Process B To a slurry of sodium hydride (11.2 g of a 60% dispersion in mineral oil) in N,N-dimethylformamide (DMF) (150 ml) under a nitrogen blanket, a solution of 1,2,4-triazole (20 g) in 150 ml of DMF was added dropwise at a rate maintaining the temperature at 30° C. or less. After about two hours of stirring, the reaction mixture became a solution.

At this point, 2-t-butyl-2-[1,3-benzodioxol-5-yl) ethyl oxirane (47.2 g) was added. The reaction mixture was stirred at room temperature for one hour, then gradually heated to 58° C. and refluxed for 64 hours. After this, distillation removed most of the DMF. The residue was then triturated in water to yield a solid, which was then dissolved in ethyl acetate (500 ml) and treated with activated charcoal, dried over anhydrous magnesium sulfate, and then concentrated to 57.9 g of a beige solid crude product.

¹H NMR (CDCl₃) analysis indicated a mixture of the title compound (70%) and the starting oxirane (30%). Trituration in hexane (200 ml) yielded 35.2 g, or 58.4%, of alpha-[2-(1,3-benzodioxol-5-yl)ethyl]-alpha-1,1-dimethylethyl-2-(1H-1,2,4-triazol-1-yl] ethanol, as an off-white solid, mp 115°–117° C. NMR data for this compound is displayed in Table 2.

The other compounds listed in Table 2 were prepared using procedures similar to the procedure described.

TABLE 2

$$R^2-CH_2-CH_2-\underset{\underset{R^1}{|}}{\overset{\overset{OH}{|}}{C}}-CH_2-N\overset{X}{\underset{}{\diagdown}}\hspace{-2pt}\diagup\hspace{-6pt}\diagdown_N$$

| No. | R₂ | R₁ | X | m.p.(°C.) | NMR Data (CDCl₃, ppm) |
|---|---|---|---|---|---|
| 14 | pyridyl | t-butyl | N | 90–91.5 | 1.03 (S, 9H), 2.10(m, 4H), 4.33(d, 2H) 7.23 (S, broad, 1H), 7.83(S, 1H), 8.33(S, 1H) |
| 15 | biphenyl | t-butyl | N | 78–83 | 1.05(S, 9H), 1.90(m, 4H), 3.17 (S, broad, 1H) 4.38(S, 2H) 7.57–7.10 (m, 9H), 8.30(S, 1H), 8.24(S, 1H) |
| 16 | 1,3-benzodioxol-5-yl | t-butyl | N | 115–117 | 1.03(S, 9H), 1.80(m, 2H), 2.39(m, 2H), 2.97(S, 1H), 4.34(S, 2H), 5.89(S, 2H), 6.45(d, 1H), 6.53(S, 1H), 6.67(d, 1H), 8.00(S, 1H), 8.20(S, 1H) |
| 17 | naphthyl | t-butyl | N | 74–82 | 1.04(S, 9H), 1.8(m, 1H), 2.05(m, 1H), 2.26(m, 1H), 3.05(m, 1H), 3.47 (S, broad, 1H), 4.41(S, 2H) 7.15–7.46 (m, 7H), 8.06(S, 1H), 8.25(S, 1H) |
| 18 | naphthyl | t-butyl | N | 92–94 | 1.05(S, 9H), 1.75–2.00(m, 3H), 2.60(m.1H), 3.11(S, 1H), 4.38(S.2H), 7.18(d, 1H), 7.43(m, 3H), 7.75(m, 3H), 8.03(S, 1H), 8.23(S, 1H) |
| 19 | 1,3-benzodioxol-5-yl | t-butyl | —CH— | 94–96 | 1.02(S, 9H), 1.75(m, 1H), 2.19(S, broad, 1H), 4.06(q, 2H), 5.88 (S, 2H), 6.46(m, 2H), 6.66(d, 1H, J=7.8Hz), 7.07(S, 2H), 7.61(S, 1H) |
| 20 | 1,4-benzodioxin-6-yl | t-butyl | —CH— | 160–162 | 1.02(S, 9H), 1.74(m, 4H), 1.84(S, broad, 1H), 4.06(q, 2H), 4.21(S, 4H), 6.49(dd, 1H, J=2.13 and 9.0 Hz), 6.55(d, 1H, J=2.13Hz), 6.73(d, 1H, J=8.22Hz), 7.08(d, 2H, J=4.7Hz), 7.60(S, 1H) |
| 21 | 1,4-benzodioxin-6-yl | t-butyl | N | 80–83 | 1.02(S, 9H), 1.70(m, 3H), 2.38(m, 1H), 3.11(S, broad, 1H), 4.22(S, 4H), 4.34(S, 2H), 6.48 (dd, 1H, J=8.22 and 1.95 Hz), 6.54(d, 1H, J=1.95Hz), 6.71(d, 1H, J=8.22Hz), 7.98(S, 1H), 8.20(S, 1H) |

Example 4

Preparation of 2-tert-butyl-2-[1,3-benzodioxol-5-yl]ethyl oxirane (Intermediate Compound 24, Table 3)

A mixture of dimethyl sulfate (28 ml) in acetonitrile (60 ml) was stirred and cooled to 10° C. A solution of dimethyl sulfide (24 ml) in acetonitrile (20 ml) was then added dropwise to this mixture at a rate which maintained the temperature below 38° C. After stirring overnight, 1-(1,3-benzodioxol-5-yl)-4,4-dimethyl-3-pentanone (23.4 g) was added in one portion, followed by the addition of sodium methoxde (16.5 g) in three portions.

After the reaction mixture was again stirred overnight, it was heated to distill off dimethyl sulfide and acetonitrile. The reside was then dissolved in ethyl acetate (200 ml), washed with water, dried over anhydrous magnesium sulfate, and concentrated to yield a crude reaction product.

¹H NMR analysis indicated a 66.6% conversion to the title compound. Further treatment of the crude product with the same amount of dimethylsulfonium methylide formed in situ completed the conversion and yielded 25 g of the title compound. NMR data for the final product is presented in Table 3 below.

Table 3 also contains information on additional oxiranes prepared as intermediates, using essentially the same procedures.

TABLE 3

$$CH_3-\underset{\underset{CH_3}{|}}{\overset{\overset{CH_3}{|}}{C}}-\overset{O}{\underset{CH_2CH_2R^2}{\triangle}}$$

| No. | R² | m.p.(°C.) | NMR Data (CDCl₃, ppm) |
|---|---|---|---|
| 22 | 2-pyridyl | liquid | 0.97(S, 9H), 2.67(m, 3H), 2.76(d, 1H, J=4.2Hz), 7.13(m, 2H), 7.57(m, 1H), 8.52(d, 1H) |
| 23 | 4-biphenyl | liquid | 1.03(S, 9H), 2.15(m, 2H), 2.60(m, 2H), 2.73 (d, 1H, J=4.17Hz), 2.83(d, 1H, J=4.14Hz), 7.54 (m, 4H) |
| 24 | 1,3-benzodioxol-5-yl | liquid | 0.97(S, 9H), 2.09(m, 2H), 2.45(m, 2H), 2.64 (d, 1H, J=4.35Hz), 2.76(d, 1H, J=4.20Hz), 5.90(S, 2H), 6.75–6.55(m, 3H) |
| 25 | 1-naphthyl | liquid | 1.01(S, 9H), 2.23(m, 2H), 2.84(d, 1H, J=4.17Hz), 2.88(d, 1H, J=4.17Hz), 2.89 (m, 1H), 3.05(m, 1H), 7.36–8.05(m, 7H) |
| 26 | 2-naphthyl | liquid | 1.02(S, 9H), 2.2(m, 2H), 2.7(m, 2H), 2.74 (d, 1H, J=4.14Hz), 2.82(d, 1H, J=4.14Hz), 7.3–7.8(m, 7H) |
| 27 | 1,4-benzodioxan-6-yl | liquid | 0.96(S, 9H), 2.05(m, 2H), 2.42(m, 2H), 2.65 (d, 1H, J=4.17Hz), 2.76(d, 1H, J=4.17Hz), 6.76–6.69(m, 3H) |
| 28 | 4-CF₃-phenyl | liquid | 0.98(S, 9H), 2.08(m, 2H), 2.57(m, 2H), 2.66(d,1H, J=4.17 Hz), 2.80(d, 1H, J=4.17Hz), 7.29(d, 2H, J=8.04Hz), 7.53(d, 2H, J=8.01Hz) |

Example 5

Preparation of 1-(1,3-benzodioxol-5-yl)-4,4-dimethyl-3-pentanone (Intermediate Compound 31, Table 4)

A solution of 1-(1,3-benzodioxol-5-yl)-4,4-dimethyl-1-penten-3-one (23 g) in ethyl acetate (125 ml) was hydrogenated over Raney nickel (6.5 g) in a 500 ml Paar flask at 17 lbs per square inch until the hydrogen absorbtion ceased. The catalyst was removed by filtration. The filtrate was concentrated and yielded 23.6 g of colorless liquid product. ¹H NMR data for this compound and for other ketone intermediates made by essentially the same procedures are presented in Table 4 below.

TABLE 4

$$CH_3-\underset{\underset{CH_3}{|}}{\overset{\overset{CH_3}{|}}{C}}-\overset{\overset{O}{\|}}{C}CH_2CH_2R^2$$

| No. | R² | m.p.(b.p.)(°C.) | NMR DATA (CDCl₃, ppm) |
|---|---|---|---|
| 29 | 2-pyridyl | (76–78/0.09 mm) | 1.11(S, 9H), 3.00(m, 4H) |

TABLE 4-continued $$CH_3-\underset{\underset{CH_3}{|}}{\overset{\overset{CH_3}{|}}{C}}-\overset{\overset{O}{\|}}{C}CH_2CH_2R^2$$

| No. | R² | m.p.(b.p.)(°C.) | NMR DATA (CDCl₃, ppm) |
|---|---|---|---|
| 30 | biphenyl | 48–50 | 1.15(S, 9H), 2.87(m, 4H), 7.44(m, 9H) |
| 31 | benzodioxole | liquid | 1.10(S, 9H), 2.76(m, 4H), 5.91(S, 2H), 6.70(m, 3H) |
| 32 | naphthyl | liquid | 1.13(S, 9H), 2.94(t, 2H), 3.37(t, 2H), 7.37–8.02(m, 7H) |
| 33 | naphthyl | 60–62 | 1.13(S, 9H), 2.90(t, 2H), 3.06(t, 2H), 7.33–7.80(m, 7H) |
| 34 | benzodioxane | liquid | 1.10(S, 9H), 2.75(S, 4H), 4.22(S, 4H), 6.74–6.68(m, 3H) |
| 35 | 4-CF₃-phenyl | liquid | 1.10(S, 9H), 2.81(t, 2H), 2.93(t, 2H), 7.29(d, 2H, J=7.92Hz), 7.52(d, 2H, J=8.01Hz) |

Example 6

Preparation of 1-(1,3-benzodioxol-5-yl)-4,4-dimethyl-1-penten-3-one (Intermediate Compound 38, Table 5)

To a mixture of pinacolone (55 g) and piperonal (75 g) in ethanol (200 ml) was added a sodium hydroxide (5.0 g) in water (115 ml) solution. The mixture solidified after stirring at room temperature for 2 days. Filtration collected 137 g of solid which was then dissolved in ethyl acetate (500 ml), washed with water (500 ml), and dried over anhydrous magnesium sulfate. Concentration and trituration in hexane yielded 104.5 g of colorless solid product, mp 94°–96° C. Using essentially the same procedures, additional alpha, beta-unsaturated ketones were prepared as intermediates and are listed in Table 5. [see Pace, E, Atti Acad Lincei, [6], 9, 778 (1929); Chemical Abstracts, 23, 4942, 1929].

TABLE 5

$$CH_3-\underset{\underset{CH_3}{|}}{\overset{\overset{CH_3}{|}}{C}}-\overset{\overset{O}{\|}}{C}CH=CH-R$$

| No. | R | m.p.(b.p.)(°C.) | NMR DATA (CDCl₃, ppm) |
|---|---|---|---|
| 36 | pyridyl | (115/0.15 mm) $n_D^{26}$ 1.5380 | 1.36(S, 9H), 7.41(d, 1H, J=7.41Hz), 7.66(d, 1H, J-6.42Hz) 7.18–7.74(m, 3H), 8.65(m, 1H) |
| 37 | biphenyl | 106–107 | 1.25(S, 9H), 7.16(d, 1H, J=15.57Hz) 7.36–7.46(m, 10H) |

TABLE 5-continued $$CH_3-\underset{\underset{CH_3}{|}}{\overset{\overset{CH_3}{|}}{C}}-\overset{\overset{O}{\|}}{C}CH=CH-R$$

| No. | R | m.p.(b.p.)(°C.) | NMR DATA (CDCl$_3$, ppm) |
|---|---|---|---|
| 38 | benzo[1,3]dioxole | 94–96 | 1.22(S, 9H), 6.01(S, 2H), 6.96(d, 1H J=15.5Hz), 7.60(d, 1H, J=15.5Hz), 6.80–7.10(m, 3H) |
| 39 | 1-naphthyl | 105–107 | 1.28(S, 9H), 7.21(d, 1H, J=15.36Hz), 7.43–8.24(m, 7H), 8.54(d, 1H, J=15.36Hz) |
| 40 | 2-naphthyl | 120–122 | 1.27(S, 9H), 7.25(d, 1H, J=15.57Hz), 7.50–7.98(m, 8H) |
| 41 | 2,3-dihydro-1,4-benzodioxin | liquid | 1.20(S, 9H), 4.28(S, 4H), 6.86(d, 1H, J=8.28Hz), 6.97(d, 1H, J=15.57Hz), 7.1–7.4(m, 2H), 7.57(d, 1H, J=15.45Hz) |
| 42 | 4-(trifluoromethyl)phenyl | 68–70 | 1.24(S, 9H), 7.18(d, 1H, J=15.7Hz), 7.66(m, 5H) |

The compounds listed in Tables 3, 4 and 5 are representative of intermediates useful in the preparation of some of the fungicidally active compounds of this invention.

Example 7

Preparation of Fungicidal Compositions

Certain of the compounds listed in Tables 1 and 2 above, were each dissolved in acetone or other suitable solvent (0.3 g. of each of the compounds in 10 ml. of acetone or other suitable solvent). One or two drops of an emulsifying agent, Triton® X-100, and water were added to the solution to form an emulsion. The amount of water added was a function of the desired concentration of the emulsion composition, reported in milligrams per liter (mg/l).

Example 8

Control of Powdery Mildew Fungus by Systemic Root Uptake

The fungicidal compositions prepared in Example 7 above, were tested to evaluate their effectiveness in preventing or controlling powdery mildew disease of barley caused by the fungus, *Erysiphe graminis* and powdery mildew disease of cucumber caused by the fungus, *Erysiphe cichoracearum*. This prevention or control capability was tested by utilizing the compounds of the present invention to control these diseases by systemic root uptake.

Pots (4×4×3.5 inches) containing 10 plants of barley (Variety "Herta") or 10 plants of cucumber (Variety "Marketmore 70") were grown to an age of six days and ten days, respectively. Upon reaching these ages, emulsion compositions (45 ml.) formed in accordance with the procedure of Example 7, were added to each pot. That is, 45 ml. of an emulsion composition of each of the compounds tested was separately added to pots containing 10 barley plants or 10 cucumber plants. The 45 ml. of emulsion composition saturated the soil in each pot without significant loss through drainage into the saucers below the pots. Each of the compositions contained a test compound in a concentration of 250 milligrams of the compound per liter of water (mg/l). A number of pots containing the same barley and cucumber plants were left untreated as controls.

The barley and cucumber plants in all the pots, including those treated and those untreated, were inoculated with powdery mildew fungus 24 hours after treatment with the emulsion composition. Fungus inoculation was accomplished by tapping leaves of previously infected barley and cucumber plants over the treated and untreated pots containing the barley and cucumber plants, respectively, to distribute spores of the fungus over the plants growing in the pots.

Six days after inoculation, disease control was evaluated on a 0 to 6 rating scale. A 0 rating was assigned when no disease was evidenced. A 6 rating was given for severe disease. Intermediate ratings were assigned depending on the degree of disease. Percent control was computed by comparing the ratings of the treated and untreated plants.

The results of this test are listed in Table 6A below, wherein systemic control of powdery mildew disease in barley is reported under the heading "BMS 250." Control of cucumber powdery mildew disease is reported in Table 6A under the heading "CMS 250."

Example 9

Control of Powdery Mildew Fungus by Foliar Application

Eight plants of barley (Variety "Larker") were planted in a pot. The number of pots, as in Example 8, was sufficient to accommodate testing in duplicate or triplicate of each of the compositions prepared in Example 7 above. This number included a duplicate number of pots, each containing eight plants, which acted as controls.

In this test each of the tested compounds was formulated into an emulsion composition as described in Example 7 above, at a concentration of 1,000 milligrams of test compound per liter of water (1,000 mg/l). These emulsions were then sprayed onto the foliage of the barley plants. The pots in which the plants were unsprayed acted as controls. The number of pots which were unsprayed equalled the number sprayed.

After the foliage of the sprayed pots was dried, the pots containing the sprayed and the unsprayed plants were all placed in a greenhouse maintained at 21° C. All the plants in the pots were then inoculated with barley powdery mildew fungus, *Erysiphe graminis*. Inoculation of the fungus was accomplished by distributing spores of the fungus over the leaves of the plants to be tested from plants which had previously been infected with the disease.

Five days after inoculation, the plants were evaluated and assigned a disease rating of 0 to 6 in accordance with the criteria explained in Example 8 above. Percentage control was computed in accordance with the procedure described in Example 8. The results of these tests are summarized in Table 6A under the heading "BMP 1,000."

Similarly, pinto bean plants were prepared, treated and inoculated with *Erysiphe Polygoni* as described above. Results of these tests are listed in Table 6A under the heading "PMP 1000".

Example 10

Control of Rice Blast Disease by Foliar Treatment

Five rice plants (Variety "Bellemont") were grown in a plurality of pots. The number of pots utilized equalled two times the number of the compositions tested plus a control for each replication of the test. The non-control pots were sprayed with emulsion compositions, prepared in accordance with the procedure of Example 7, wherein each test compound was provided in a concentration of 1,000 mg/l. This spraying occurred 3 to 4 weeks after planting of the plants in the pots. The controls remained unsprayed.

The sprayed and unsprayed plants, five to a pot, were inoculated with spores of the rice blast fungus, *Pyricularia oryzae*. This inoculation was accomplished by preparing inoculum containing 20,000 to 30,000 spores per milliliter. The inoculum was sprayed onto the plants to which one or two drops of ethoxylated sorbitan monolaurate surfactant had been earlier applied to ensure proper wetting of the inoculum onto the plant foliage.

The inoculated plants in the control and non-control pots were incubated in a control chamber, at a humidity of 99% and a temperature of 21° C., for about 24 hours to allow infection to occur. The plants, after 24 hours in the control chamber, were transferred to a greenhouse for six days to permit disease development to occur. Disease was manifested by blast lesions on the leaves. Disease control was calculated by one of two methods. In one method the number of lesions were counted, if infection was moderate. Alternatively, in the case of severe infection, disease was evaluated by the 0 to 6 rating system discussed in Example 8. The disease control rating system employed to determine disease control of any particular test compound was also utilized in evaluating its control.

The results of these tests are listed in Table 6B below under the heading "RCB 1000".

Example 11

Control of Bean Rust Fungus Eradicant Test

Two pinto bean plants, *P. vulgaris*, were planted in a plurality of pots. When the plants were seven days old, at the primary leaf stage of growth, they were all sprayed with a suspension containing 20,000 spores of the bean rust fungus, *Uromyces phaseoli*, per milliliter of suspending water. All the pots containing the inoculated plants were then incubated in a controlled environmental chamber, maintained at 99% humidity and 21° C., for 24 hours to allow infection to develop. The plants were then removed from the incubator and allowed to dry. Two days after inoculation the infected plants were sprayed with compositions prepared in accordance with the procedure of Example 7 to provide a dosage of 1,000 mg/l of each test compound. An equal number of infected plants were not sprayed and used as controls. All the sprayed and unsprayed plants were placed in a greenhouse, maintained at a temperature of 21° C., for five days to allow any disease present to be expressed. The sprayed and control plants were assessed for disease using the 0 to 6 rating system described in Example 8. Disease control, as discussed in Example 8, was then determined. The control of disease, expressed as percent reduction of disease, is listed in Table 6A under the heading "BRE 1000".

Example 12

Control of Peanut Cercospora Leafspot by Foliar Treatment

Four Virginia peanut plants were grown in each of a plurality of pots. Enough pots were prepared so that each of the test compositions, prepared as emulsion compositions in accordance with the procedure of Example 7, could be evaluated by spraying each of the test compositions on the four plants of one pot. An equal number of pots, which were not sprayed, were provided as controls. Spraying occurred when the plants were four weeks old. The concentration of the emulsion utilized to spray the peanut plants was 900 mg/l.

All the plants, both sprayed and unsprayed (the controls), were thereafter inoculated with spores of Peanut Cercospora leafspot, *Cercospora arachidicola*. The inoculum contained 20,000 to 30,000 spores per milliliter. The inoculum (which had been previously treated with one or two drops of ethoxylated sorbitan monolaurate to aid in wetting the leaves) was sprayed onto the leaves of the peanut plants. All the pots containing the inoculated peanut plants were incubated in a control chamber, maintained at 24° C., for 36 hours to develop infection. The plants were then placed in a greenhouse for 21 days to allow disease development.

After 21 days in the greenhouse, all the plants were taken out and evaluated using the 0 to 6 disease rating system. Percent control was computed as described in Example 8.

21

The results of these tests are reported in Table 6B under the heading "PNT 900".

Example 13

Control of Barley Blast by Foliar Treatment

A plurality of pots which included 10 plants of 6 day old barley (Variety "Herta") were prepared. These pots were sprayed with emulsion compositions, formulated in accordance with the procedure of Example 7.

The plants in these pots, plus an equal number of 6 day old Variety "Herta" barley plants in control pots, which were unsprayed, were inoculated with spores of the blast fungus, *Pyricularia oryzae*. The method of inoculation utilized was the same as that described in Example 10, which employed the same fungus.

All the inoculated plants were placed in a greenhouse, maintained at a temperature of 21° C. for five days. At that time, the plants were evaluated using the 0 to 6 disease rating system described above. Percent control was computed and the results of these tests are reported in Table 6A under the heading "BBL 1000".

Example 14

Control of Barley Spot Blotch by Foliar Treatment

A plurality of pots which included 10 plants of 6 day old barley (Variety "Robust") were prepared. These pots were sprayed with emulsion compostions, formulated in accordance with the procedure of Example 7.

The plants in these pots, plus an equal number of 6 day old Variety "Robust" barley plants in control pots, which were unsprayed, were inoculated with spores of the blotch fungus, *Helminthosporium Sativuum*. The method of inoculation utilized was the same as that described in Example 10.

All the inoculated plants were placed in a greenhouse, maintained at a temperature of 21° C. for five days. At that time, the plants were evaluated using the 0 to 6 disease rating system described above. Percent control was computed and the results of these tests are reported in Table 6B under the heading "HSAT 1000".

Example 15

Control of Twelve Fungus Species

Certain of the compounds listed in Tables 1 and 2, were each solubilized in acetone at a concentration of 500 mg/l. Filter paper discs, each 11 mm. in diameter, were dipped in each of the test solutions. The discs were allowed to dry in air to drive off the acetone solvent. An equal number of discs were untreated and acted as controls.

Each of the treated and untreated discs were then placed on agar plates and eleven fungus species: *Alternaria solani* (ALT), *Botrytis cinerea* (BOT), *Fusarium oxysporum* (FUS), *Phytophthora infestans* (PHY), *Sclerotinia sclerotiorum* (SCM), *Sclerotium rolfsii* (SCO), *Colletotrichum gossypii* (COLL), *Cercosporidium personatum* (COSP), *Pythium ultimum* (PYTH), *Rhizoctonia solani* (RHIZ), and *Septoria nodorum* (SEPT), were added to the center of each disc in the form of a culture plug with the fungus mat in contact with the treated paper of the test disc or, in the case of the controls, in contact with the untreated test paper. The plates were incubated at 29° C. in an oven.

Percent growth inhibition of the eleven fungus species by the tests compounds was evaluated, after incubation, by comparing the measurement of the radius from the center of the fungus colony of the treated discs to the measurement of the radius from the center of the fungus colony of the untreated discs. The results of these tests appear in Tables 6A and 6B under the headings "ALT 500," "BOT 500," "FUS 500", "PHY 500", "SCM 500", "SCO 500", "COLL 1000", "COSP 500", "PYTH 500", "RHIZ 500" and "SEPT 500".

A separate test was utilized to determine the control of the fungi species, *Cercospora arachidicola* (CER). In this test two drops of the fungus were added as a spore suspension (20,000 spores per milliliter) to the chemically treated discs, rather than as a mycelial culture plug. Scoring of the effectiveness of the compounds in controlling the *Cercospora arachidicola* fungus was determined with control based on the following scoring criteria: 100 represented complete inhibition of germination and growth of the fungus; 80 represented nearly complete inhibition but some growth of the fungus; 50 represented partial inhibition of growth or early complete inhibition with later growth; 20 indicated some, but not significant, inhibition of growth; and 0 indicated complete growth of the fungus without any inhibition.

The results of the tests involving *Cercospora arachidicola*, are reported in Table 6A below under the heading "CER 500".

TABLE 6A

| | PERCENT FUNGICIDAL CONTROL | | | | | | | | | | |
|---|---|---|---|---|---|---|---|---|---|---|---|
| No. | ALT 500 | BBL 1000 | BMP 1000 | BMS 250 | BOT 500 | BRE 1000 | CER 500 | CMS 250 | FUS 500 | PHY 500 | PMP 1000 |
| 1 | 70 | 100 | 100 | 100 | 0 | 0 | 0 | 100 | 100 | 100 | 0 |
| 2 | 60 | 100 | 100 | 0 | 80 | 25 | 0 | 0 | 0 | 0 | 70 |
| 3 | 80 | 100 | 100 | 100 | 100 | 0 | 100 | 100 | 60 | 0 | 0 |
| 5 | 50 | 85 | 100 | 100 | 100 | 0 | 0 | 100 | 100 | 65 | 100 |
| 6 | 60 | 0 | 100 | 0 | 60 | 100 | 80 | 0 | 30 | 50 | 100 |
| 7 | 55 | 100 | 100 | 0 | 60 | 0 | 100 | 0 | 40 | 10 | 0 |
| 9 | 30 | 0 | 0 | 0 | 60 | 0 | 0 | 0 | 90 | 10 | 0 |
| 10 | — | 65 | 50 | 0 | 50 | 0 | — | 0 | 65 | — | 0 |
| 11 | — | 100 | 100 | 0 | 85 | 95 | — | 0 | 45 | — | 80 |
| 12 | — | 80 | 100 | 0 | 55 | 70 | — | 15 | 50 | — | 10 |
| 13 | — | 50 | 0 | 100 | 0 | — | — | 100 | 20 | — | 90 |

TABLE 6A-continued

PERCENT FUNGICIDAL CONTROL

| No. | ALT 500 | BBL 1000 | BMP 1000 | BMS 250 | BOT 500 | BRE 1000 | CER 500 | CMS 250 | FUS 500 | PHY 500 | PMP 1000 |
|---|---|---|---|---|---|---|---|---|---|---|---|
| 15 | 35 | 100 | 100 | 0 | 0 | 100 | — | 70 | 100 | — | 75 |
| 16 | 90 | 100 | 100 | 100 | 100 | 80 | — | 100 | 100 | — | 50 |
| 17 | 85 | 100 | 0 | 0 | 0 | — | — | 85 | 0 | — | 0 |
| 18 | 100 | 100 | 50 | 0 | 15 | 100 | — | 0 | 5 | — | 50 |
| 19 | — | — | 85 | 100 | 0 | 90 | — | 100 | 0 | — | 90 |
| 20 | — | — | 0 | 0 | 0 | 0 | — | 0 | 5 | — | 0 |
| 21 | — | — | 50 | 15 | 0 | 80 | — | 100 | 80 | — | 0 |

TABLE 6B

PERCENT FUNGICIDAL CONTROL

| No. | SCM 500 | SCO 500 | COLL 1000 | COSP 500 | HSAT 1000 | PYTH 500 | SEPT 500 | RHIZ 500 | PNT 900 | RCB 1000 |
|---|---|---|---|---|---|---|---|---|---|---|
| 1 | 60 | 100 | — | — | 100 | — | — | — | — | 25 |
| 2 | 0 | 0 | — | — | 65 | — | — | — | — | 0 |
| 3 | 30 | 100 | — | — | 100 | — | — | — | — | 74 @ 300 PPM |
| 5 | 50 | 70 | — | — | 70 | — | — | — | — | 10 |
| 6 | 40 | 80 | — | — | 55 | — | — | — | — | 0 |
| 7 | 30 | 5 | 100 | — | — | — | — | — | 88 | 92 @ 300 PPM |
| 9 | 55 | 90 | 45 | — | 45 | — | — | — | — | — |
| 10 | — | 90 | 50 | 80 | 0 | — | 70 | — | — | — |
| 11 | — | 5 | 85 | 100 | 100 | — | 100 | — | — | — |
| 12 | 35 | 5 | 65 | 100 | 85 | — | 85 | — | — | — |
| 13 | — | 5 | 25 | 100 | 65 | — | 40 | — | — | — |
| 15 | — | 70 | 40 | — | 100 | 20 | — | 40 | — | — |
| 16 | — | 90 | 100 | 0 | 100 | 0 | — | 50 | — | — |
| 17 | — | 5 | 0 | 0 | 100 | 20 | — | 10 | — | — |
| 18 | — | 10 | 5 | 100 | 90 | 5 | — | 15 | — | — |
| 19 | 0 | — | 95 | 0 | 100 | 0 | 100 | 0 | — | 70 |
| 20 | 65 | — | 65 | 0 | 60 | 5 | 80 | 0 | — | 70 |
| 21 | 50 | — | 75 | 100 | 80 | 0 | 5 | 0 | — | 35 |

What is claimed is:

1. A compound having the formula

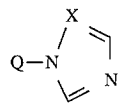

wherein Q is

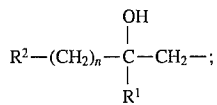

$R^1$ is $C_1$–$C_8$ alkyl;

$R^2$ is

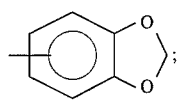

X is nitrogen; and n is 2, 3 or 4, or a stereoisomer thereof.

2. A compound as recited in claim 1 wherein n is 2.

3. A compound as recited in claim 2 wherein $R^1$ is a $C_3$–$C_6$ alkyl.

4. A compound as recited in claim 3 wherein $R^1$ is a $C_3$–$C_6$ branched alkyl.

5. A compound as recited in claim 4 wherein $R^1$ is t-butyl.

6. A fungicidal composition comprising: (a) a fungicidally effective amount of a compound as recited in claim 1 and (b) a suitable carrier.

7. A method for controlling undesirable fungi at a loci to be protected, which comprises applying a fungicidally effective amount of a compound as recited in claim 1 to the loci to be protected.

8. A method for controlling phytopathogenic fungi on a plant to be protected, which comprises applying a fungicidally effective amount of a compound as recited in claim 1 to the soil in which the plant is grown.

9. A method for controlling undesirable fungi at a loci to be protected, which comprises applying a fungicidally effective amount of a compound as recited in claim 1 to the seeds of the plant prior to planting.

* * * * *